United States Patent
Austin

[11] Patent Number: 5,184,619
[45] Date of Patent: Feb. 9, 1993

[54] INTRAUTERINE PRESSURE AND FETAL HEART RATE SENSOR

[75] Inventor: Sandor Austin, Edina, Minn.

[73] Assignee: Peritronics Medical, Inc., Brea, Calif.

[21] Appl. No.: 103,651

[22] Filed: Oct. 2, 1987

Related U.S. Application Data

[63] Continuation-in-part of Ser. No. 929,639, Nov. 10, 1986, abandoned.

[51] Int. Cl.$^5$ .................................................. A61B 5/04
[52] U.S. Cl. ................................... 128/639; 128/642; 128/698; 128/748; 128/775; 128/778
[58] Field of Search ............... 128/639, 642, 668, 695, 128/696, 698, 672, 673, 774, 778, 784

[56] References Cited

U.S. PATENT DOCUMENTS

| | | | |
|---|---|---|---|
| 3,326,207 | 6/1967 | Egan | 128/642 |
| 3,724,467 | 4/1973 | Avery et al. | 128/784 |
| 3,769,984 | 11/1973 | Muench | 128/419 P |
| 4,114,288 | 9/1978 | Carter et al. | 128/778 |
| 4,172,451 | 10/1979 | Kline | 128/642 |
| 4,476,871 | 10/1984 | Hon | 128/642 |
| 4,510,944 | 4/1985 | Porges | 128/687 |
| 4,554,927 | 11/1985 | Fussell | 128/673 |

OTHER PUBLICATIONS

"Tripolar HIS-Bundle Electrode" U.S. Catheter litterature Oct. 1971.

Primary Examiner—David M. Shay
Attorney, Agent, or Firm—Knobbe, Martens, Olson & Bear

[57] ABSTRACT

An apparatus for sensing intrauterine pressure and fetal heart rate. The apparatus comprises an elongated flat, flexible tubular housing; at least one electrode mounted on the housing; apparatus for connecting the electrode to apparatus for monitoring the heart rate signal. In one embodiment of the invention, apparatus for sensing intrauterine pressure is also mounted to the housing, either as a separate segment or as a part of the heart rate pickup electrode.

32 Claims, 4 Drawing Sheets

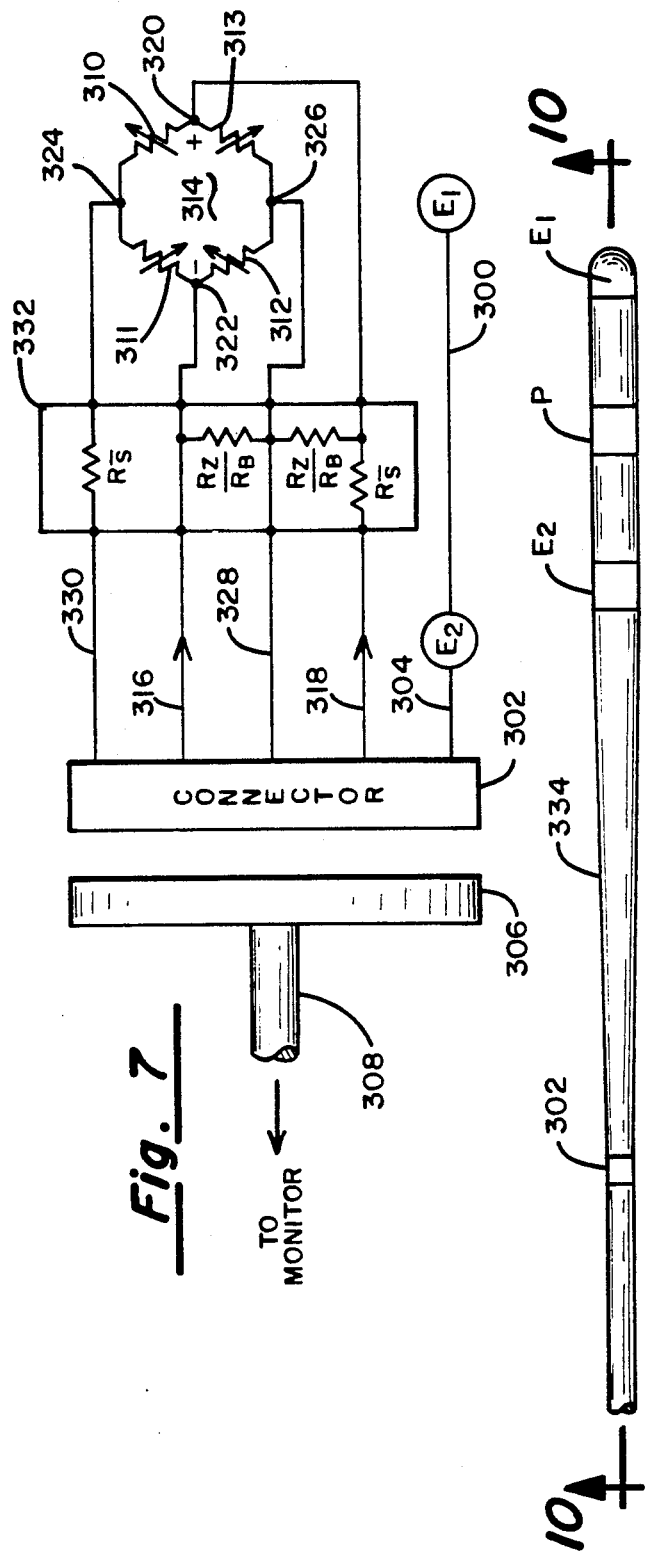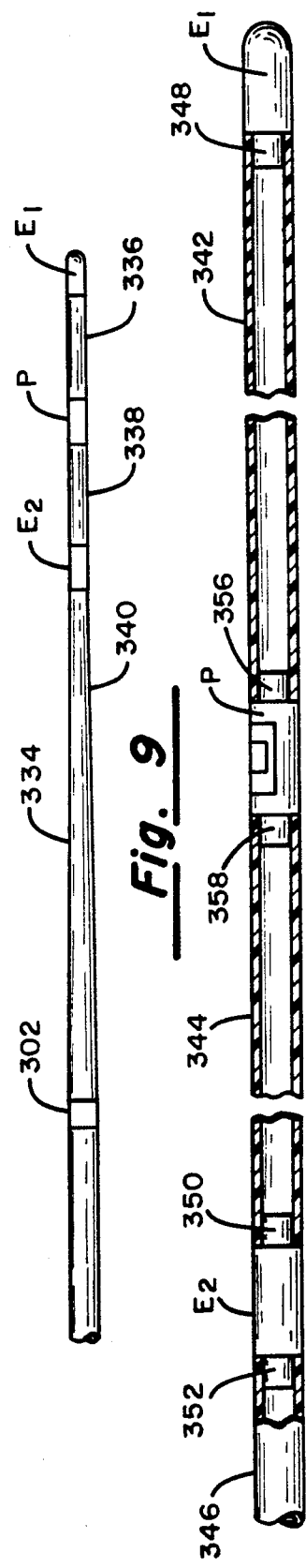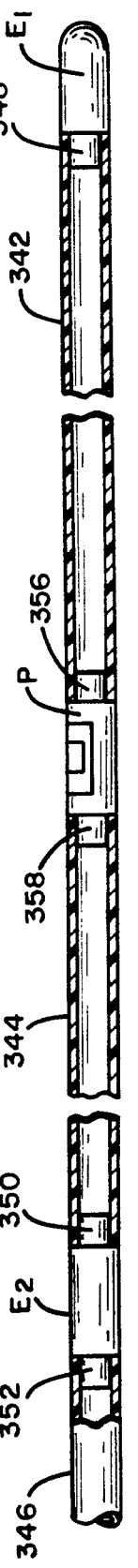

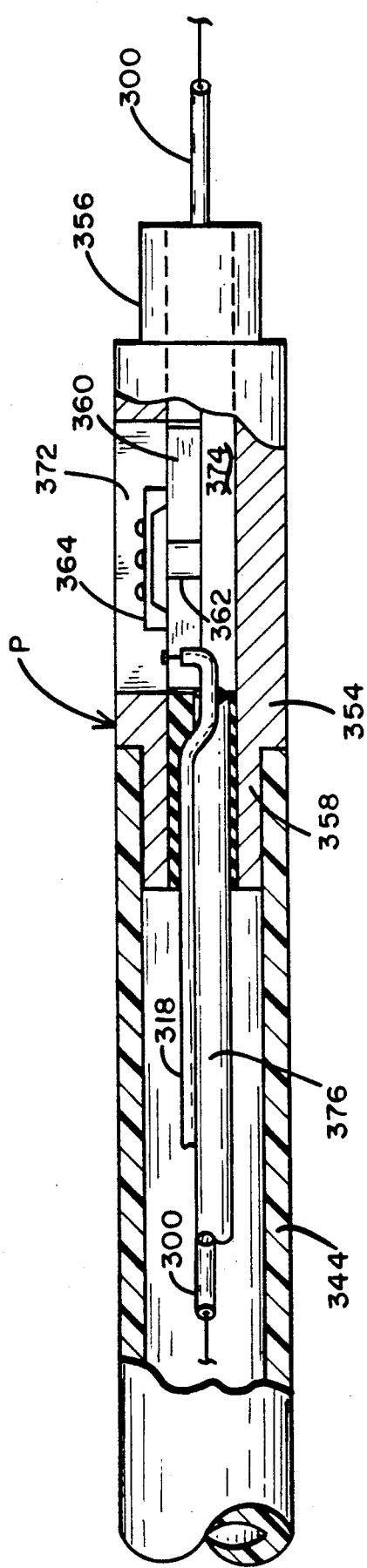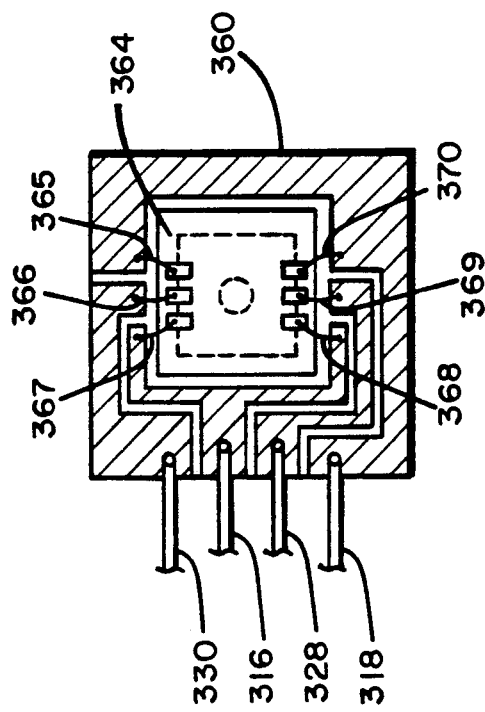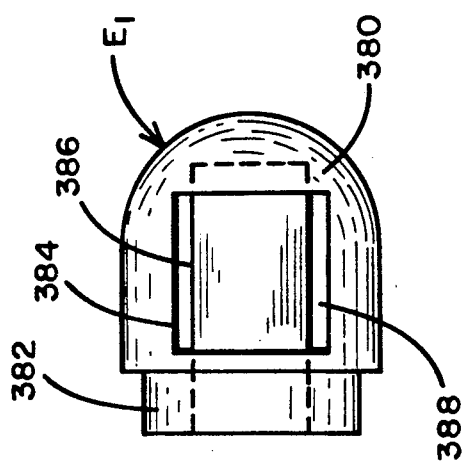

INTRAUTERINE PRESSURE AND FETAL HEART RATE SENSOR

CROSS-REFERENCE TO RELATED APPLICATIONS

This application is a continuation-in-part of application Ser. No. 929,639, filed Nov. 10, 1986 now abandoned.

BACKGROUND OF THE INVENTION

I. Field of the Invention

The present invention is directed to intrauterine pressure and fetal heart rate sensors and pressure transducers, and, more particularly to intrauterine pressure and fetal heart rate sensors and pressure transducers which are nonintrusive to the fetus during labor.

II. Discussion of the Prior Art

Presently, intrauterine pressure and fetal heart rate are monitored with two separate sensors. The fetal ECG is used in some devices, including the present invention, to determine fetal heart rate. In presently used devices, the intrauterine pressure is transmitted from the uterus to the external transducer diaphragm via a liquid column contained in various sizes of tubings. Such a liquid column is in direct contact with the amniotic fluid at its distal receiving end or through side holes in the tubing. The setup for such a system requires careful debubbling of the pressure catheter and transducer dome. Further, such a system requires frequent manual flushings for short-term applications and continuous flushing for long-term applications. Flushing is needed in such systems in order to avoid fluid coagulation in the monitoring line since the frequent contraction pressures present during labor will force the uterine fluid into the pressure tubing. In known systems, the uterine fluid contains materials which may completely clot the tubing unless the tubing is flushed frequently. Furthermore, since the prior art pressure sensor works on a hydraulic head differential principle, it requires frequent repositioning of the external transducer each time the mother changes position.

Current devices for sensing fetal ECG use positive fixation means, e.g., harpoon tip, a spiral or corkscrew-type electrodes which usually are anchored or screwed into the scalp of the fetus or a suction cup device. In certain circumstances, the placement and removal of such electrodes may result in serious and even permanent injury to the fetus. Such devices are used because prior to the invention, it was the accepted belief in the medical community that positive contact with the fetus was necessary at all times to enable sensing of the fetal ECG. It has now been discovered that fetal ECG may be sensed with the present invention whether or not direct contact is established with the body of the fetus, as long as the sensor is placed within the uterus. The uterus itself provides a conductive environment sufficient to allow monitoring of the fetal ECG, from which the fetal heart rate is derived.

Disadvantages of known pressure and fetal heart rate monitoring and sensing devices include, among other factors, considerable time to set up continual monitoring and flushing of the devices, possible excessive amount of liquid administered to the patient, increased contamination possibilities, additional cost for flushing, trauma and possible injury to the fetus and/or the uterus, additional procedure time for electrode removal and spontaneous electrode release from the fetus requiring reinsertion.

OBJECTS

It is an object of the invention to reduce fetal injuries related to the monitoring of fetal heart rate by eliminating the need for a positive fixation electrode, e.g., one involving penetration into the scalp of the fetus.

It is another object of the invention to reduce the set-up time required for fetal heart rate and intrauterine pressure sensing apparatus during labor and to provide directly sensed and transmitted pressure information.

It is yet another object of the invention to decrease contamination possibilities in a system for monitoring and sensing fetal heart rate and intrauterine pressure.

It is still another object of the invention to eliminate the need for flushing the intrauterine pressure sensing system.

It is yet another object of the invention to reduce procedure time for electrode placement and removal.

It is another object of the invention to provide an intrauterine pressure measuring device which does not require frequent adjustment each time the mother shifts position.

It is an advantage of the invention that direct contact with the body of the fetus is not required to sense fetal ECG as long as the sensor is placed within the uterus according to standard insertion techniques.

These and other objects, features and advantages of the invention will be apparent to one skilled in the art from the drawings, descriptions and claims of the invention as set out hereinbelow.

SUMMARY OF THE INVENTION

An apparatus for sensing intrauterine pressure and fetal heart rate from fetal electrocardiogram (ECG) signals is disclosed. The apparatus comprises a generally flat, elongated, tubular sheath housing suitable for insertion into the uterus and having a distal end and a proximal end. A surface electrode is mounted near the distal end of the housing and another electrode may be mounted proximal to the distal electrode and suitably distanced from it such that ECG signals are sensed in cooperation with the distal electrode. Means are provided for connecting the distal or both the distal and proximal electrodes to a means for monitoring the ECG signal. In an embodiment of the invention, electronic pressure transducing means for sensing intrauterine pressure and producing a signal proportional to the pressure is also mounted to the housing, either separate from the surface electrodes or as a component part of one of the surface electrodes.

BRIEF DESCRIPTION OF THE DRAWINGS

FIG. 7 is an electrical block diagram of an alternative embodiment of a fetal heart rate and intrauterine pressure sensing and monitoring system.

FIG. 8 is a plan view of the alternative embodiment.

FIG. 9 is a side elevation of the alternative embodiment.

FIG. 10 is an enlarged cross-sectional view taken along line 10—10 in FIG. 8.

FIG. 11 is a greatly enlarged cross-sectional view of the pressure transducer assembly.

FIG. 12 is an enlarged view of the pressure transducer assembly.

FIG. 13 illustrates the manner in which a tip electrode can be modified to contain the pressure transducer assembly.

DETAILED DESCRIPTION OF THE PREFERRED EMBODIMENT

Figure 1:
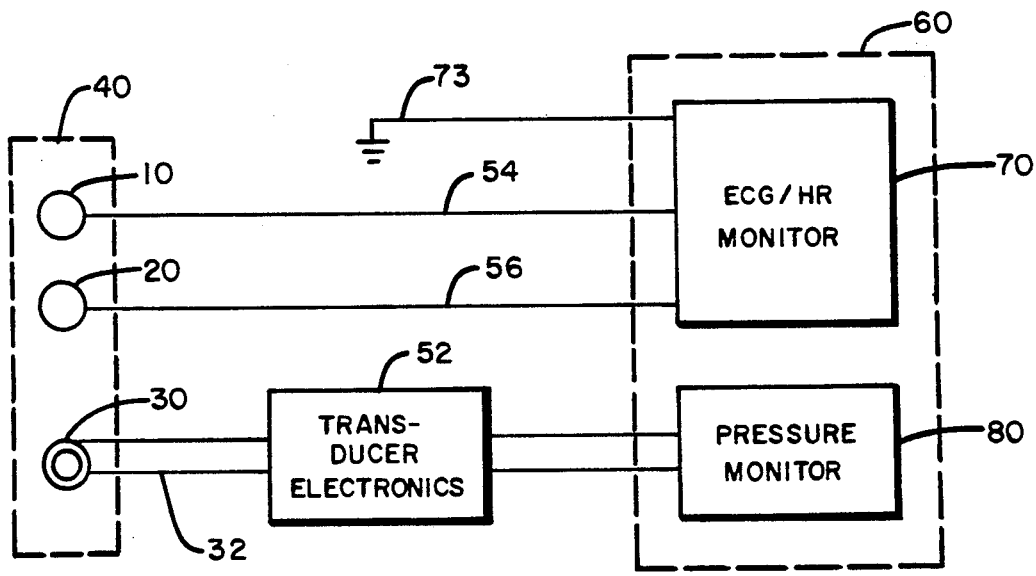
FIG. 1 shows a schematic block diagram of the electrical apparatus and wiring of one embodiment of a fetal heart rate and intrauterine pressure sensing and monitoring system.

FIG. 1 shows a schematic block diagram of the electrical apparatus and wiring of one embodiment of a fetal heart rate and intrauterine pressure sensing and monitoring system. The system comprises a sensor means 40 and monitoring means 60 connected together by standard connecting means (not shown). The sensor 40 includes a first electrode 10, pressure transducer means 30, a second electrode 20 and means for connecting the sensor to the monitoring means 60. The monitoring means 60 includes ECG and heart rate monitoring (ECG/HR) means 70 and pressure monitoring means 80.

In one embodiment of the invention, the electrodes 10 and 20 may advantageously be comprised of platinum, silver chloride, gold, stainless steel or other similar conductive metals. It will be recognized by one skilled in the art that other well-known materials may be employed as materials for the ECG pick-up electrodes 10 and 20. The electrodes 10 and 20 transmit ECG signals to the ECG/HR monitoring means 70 through conductors 54 and 56, respectively. A signal ground or reference electrode 72 is typically provided by a metal plate in contact with the mother's body, e.g., a leg plate. Such a plate is typically an integral part of the connecting means conventionally used with commercially available ECG/HR monitoring devices. Rather than utilizing a leg plate, the reference electrode may be a conventional ECG electrode. The ECG/HR monitoring means may be any commercially available unit suitable for use in perinatal care. Similarly, pressure monitoring means 80 is connected to pressure transducer electronics 52 via cable 32. Cable 32 may advantageously be a flex cable which interconnects the transducer 30, the transducer electronics 52 and the monitor 80. Cable 32 is preferably a multiconduit electrical cable suitable for transmitting electrical signals indicative of uterine pressure and providing electrical excitation to the pressure transducer. Pressure monitoring means 80 may also suitably be any commercially available monitoring device suitable for use in perinatal care. Many such devices are typically integrated into one unit for monitoring both fetal ECG and heart rate and intrauterine pressure. A typical monitoring device suitable for use with the sensor of the present invention is the Model 112 Fetal Monitor manufactured and sold by Corometrics Medical Systems, Inc. of Wallingford, Connecticut. However, other such monitors may also be used in combination with this invention.

The pressure transducer means 30 may advantageously be a miniature solid state differential pressure transducer. The transducer means includes a body, means for converting pressure signals to electrical signals (e.g. a piezoelectric crystal), means for interfacing with external pressure monitors and means for providing temperature and pressure compensation. One such transducer is readily available as an off-the-shelf item for use by other equipment manufacturers. Such miniature transducers have a pressure range of from about 0 to about 300 mmHg, a sensitivity of about 5 uV/V/mmHg within about 1% accuracy and an operating temperature range of from about 15° C. to about 40° C. One such commercially available OEM pressure transducer is the "OEMeds" (TM) sensor as manufactured by Gould Inc., Cardiovascular Products Division, of Oxnard, California. Such commercially available pressure transducers further include electronics 52 for interfacing with means for monitoring pressure 80. The electronics 52 typically comprise a sensor chip, a temperature compensating resistor chip and a flex circuit (not shown). The electronics 52 may suitably be integrated into or mounted onto connecting means (shown in FIG. 2) by well known mounting or hybrid circuit manufacturing techniques.

Figure 2:
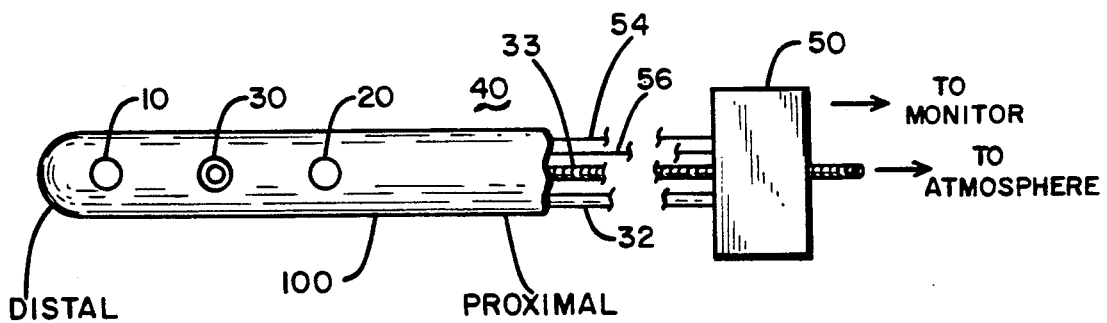
FIG. 2 shows a schematic drawing of one embodiment of a fetal heart rate and intrauterine pressure sensing apparatus.

FIG. 2 shows a schematic drawing of one embodiment of a fetal heart rate and intrauterine pressure sensing apparatus. The apparatus comprises flexible tubular housing 100, two electrodes 10 and 20 for ECG pick-up mounted on the housing 100 distal and proximal to a pressure sensing transducer 30. The electrodes are slightly protruding from the surface of the housing, having a smooth surface and an appropriate radius to assure contact. The electrodes 10 and 20 are connected with signal conductors 54 and 56 embedded within the housing to the connector 50 located on the housing's proximal end. Since the transducer 30 operates by differential means, it must be vented to the atmosphere for calibration of a reference or zero pressure reading. This venting is accomplished by means for venting 33. The venting means 33 may be a tube or lumen running from inside of the housing 100 to the atmosphere. The venting tube may run through or around the connector 50. The venting means 33 may advantageously be small-bore polyethylene tubing or a similar biocompatible material.

The housing 100 may advantageously be comprised of a flat, semi-pliable plastic or medical grade silastic which may be in the shape of a flat tube, similar in shape to a multi-conductor, flat ribbon cable commonly used for interconnecting computer components. Contained within the housing 100 are the electrode lines 54 and 56 which terminate at the connector means 50, cable 32 and venting means 33. The pressure transducer means 30 must be hermetically sealed within the housing by well-known sealing techniques. The transducer body utilized, and commercially available, may advantageously include a polycarbonate body filled with a dielectric gel (not shown).

Generally, in use, the sensor 40 is inserted between the fetus and the internal uterine wall following rupture of the membranes and using standard insertion techniques similar to well-known techniques used for inserting transcervical pressure tubing.

Figure 3:
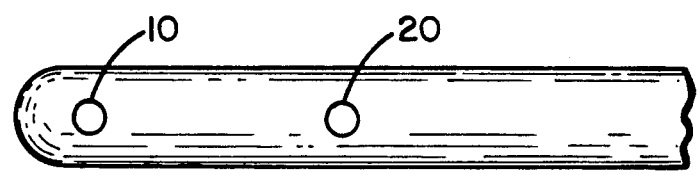
FIG. 3 shows a schematic drawing of one embodiment of a fetal heart rate sensing apparatus.

Referring now to FIG. 3, a sensor is shown for fetal heart rate measurements only. The sensor in FIG. 3 is identical to the sensor 40 described with respect to FIG. 1, except that the pressure transducer means 30 is deleted. Such a sensor would be used in situations where monitoring intrauterine pressure is not required.

Figure 4:
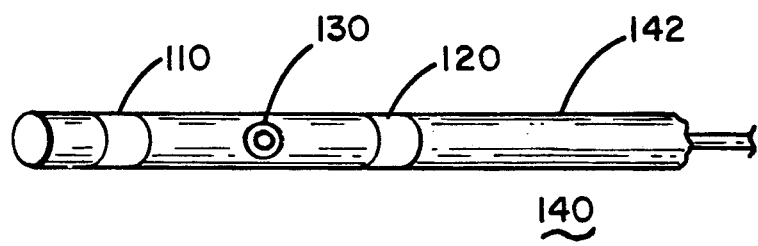
FIG. 4 shows a schematic drawing of another embodiment of a fetal heart rate and intrauterine pressure sensing apparatus having a tubular housing.

Referring now to FIG. 4, yet another embodiment of a sensor for sensing fetal heart rate and intrauterine pressure is shown. This embodiment comprises a housing 142, band or ring electrodes 110 and 120 and pressure transducer 130. The housing 142 is a tubular housing having a circular cross-section and similar to a catheter in shape. The electrodes 110 and 120 conform to the shape of the housing 142 by banding around the housing. The transducer 130 may be similar to those described hereinabove. The electrodes and transducer may be disposed as described above and comprise similar materials and components. It is not necessary for the transducer to be located between the electrodes in any of the embodiments shown. The transducer may be located distal to the first electrode, slightly recessed from the distal tip of the housing.

In one example of an embodiment of the invention according to the drawing shown in FIG. 4, the catheter diameter may be in the range of about 8 F to 12 F (French Catheter Scale), the catheter length may be in the range of 80 cm to 100 cm, and the width of the ECG electrodes may be in the range of 1 mm to 5 mm. In the aforesaid example, the elements are disposed as follows: the first electrode is about 1 cm from the distal tip of the housing, the pressure transducer is about 5 cm from the distal tip of the housing and the second electrode is about 9 cm from the distal tip of the housing.

Figure 5:
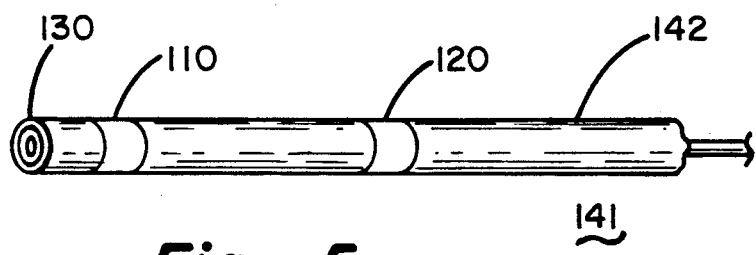
FIG. 5 shows a schematic drawing of another embodiment of a fetal heart rate and intrauterine pressure sensing apparatus having a tubular housing and the pressure transducer mounted at the distal tip of the sensor transverse to the axis of the tubular housing.

Referring now to FIG. 5, yet another embodiment of a sensor for sensing fetal heart rate and intrauterine pressure is shown. This embodiment is similar to the embodiment of FIG. 4 except that the transducer 130 is disposed transversely to the electrodes and the transducer is located at the distal tip of the sensor housing.

Figure 6:
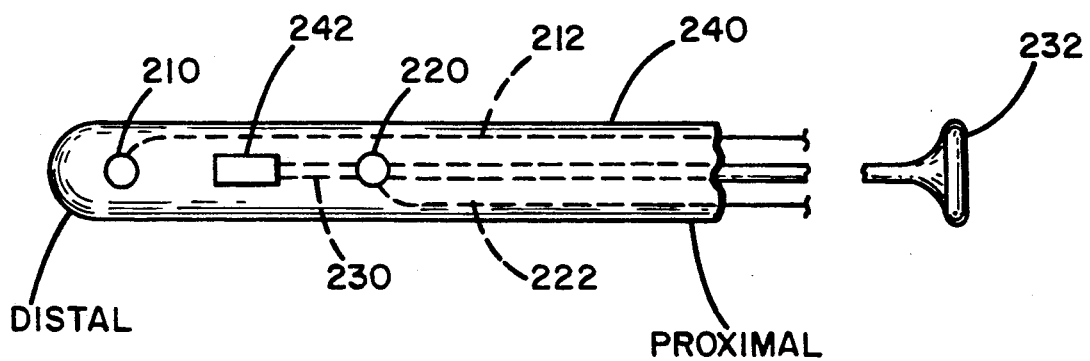
FIG. 6 shows a schematic drawing of one embodiment of a fetal heart rate and intrauterine pressure sensing and monitoring system including a pressure cavity and embedded, prefilled and sealed pressure tubing terminating in a Luer fitting.

Referring now to FIG. 6, yet another embodiment of a device for monitoring fetal ECG and intrauterine pressure is illustrated in a conceptual drawing. The device of FIG. 6 features ECG electrodes 210 and 220, pre-filled pressure tubing 230 and housing 240 having a pre-filled and sealed sensing cavity 242. The ECG electrodes 210 and 220 are similar to those electrodes described hereinabove with respect to the embodiments of FIGS. 1 and 2. Electrodes 210 and 220 are connected to an exterior ECG monitoring means (not shown) by means of conductors 212 and 222.

The pressure cavity 242 is recessed from the distal tip 214 of the house 240 and is sealed with a highly compliant . membrane such as silicon rubber. The cavity 242 is connected through tubing 230 to the proximal (outside) end of the housing 240. The tubing 230 is embedded in the housing 240 and terminates in a sealed Luer fitting 232. The pressure cavity 242 and tubing 230 are advantageously prefilled with bubble-free, sterile, biocompatible liquid and completely sealed. The biocompatible liquid may be glycerin or a similar high viscosity liquid.

With respect to each of the embodiments of the invention as described in FIGS. 1, 2, 3, 4, 5 and 6, the approximate external dimensions of the sensor units may advantageously be about 300 mm to 1000 mm in length by about 15 mm to 10 mm in width by about 3 mm maximum thickness. The preferable minimum distance between the first and second electrodes should be in the range from about 4 to 8 cm.

A still further embodiment of the present invention is illustrated in FIGS. 7 through 12 of the drawings. FIG. 7 is an electrical schematic diagram of the intrauterine pressure and fetal heart rate sensor and is seen to include first and second surface electrodes $E_1$ and $E_2$ which are connected to one another by a conductor 300 and to a proximal connector plug 302 by a conductor 304. As with the earlier described embodiments, when the electrodes $E_1$ and $E_2$ are placed within the conductive environment provided by the intrauterine fluid, ECG signals attributable to both the mother and the fetus are picked up by the electrodes and conveyed over the conductors 300 and 304 to a connector terminal in plug 302 and then through a corresponding terminal of a mating plug part 306 and thence through a multi-conductor cable 308 to a monitor (not shown). The circuitry in the monitor then is able to discriminate and isolate the fetal heart rate signal from that of the mother.

To sense the intrauterine pressure, and more appropriately, the changes in such pressure occurring due to uterine contractions, the sensor device includes a plurality of piezoresistive elements 310 through 313 connected as a Wheatstone bridge 314. The bridge 314 is adapted to be energized by signals provided over conductors 316 and 318 to oppose terminals 320 and 322 of the ridge 314. The output from the bridge is obtained across terminals 324 and 326 and is fed back over conductors 328 and 330 to the plug member 302 and thence through mating plug member 306 and the multi-conductor cable 308 to the monitor device (not shown). The monitor is capable of providing an indication of pressure variations corresponding to the voltage output obtained across terminals 324 and 326 of the bridge 314.

With continued reference to FIG. 7, there is also illustrated a compensation board 332 to which the bridge energization lines and bridge output lines connect. The resistive components on the compensation board 332 are appropriately trimmed so as to accommodate variations in the piezo-resistive elements 310 through 313 so that there will be uniformity between sensor products. The constructional features of the compensation board 332 will be explained in greater detail hereinbelow when FIGS. 11 and 12 are discussed.

FIGS. 8 and 9 are, respectively, top and side views of the intrauterine ribbon sensor of the instant embodiment. It is seen to include a flattened molded strip of a suitable medical grade plastic, preferably polyurethane or silicon rubber, on which is mounted a distal tip surface electrode $E_1$, a pressure sensor P and a proximal surface electrode $E_2$. The bridge 314 and the compensation board 332 as well as the conductors joining one to the other form part of the pressure sensor P and the conductors 304, 316, 318, 328 and 330 extend internally within the molded silicon or urethane rubber strip 334 to the proximal connector 302. To reduce noise pick-up, the conductors may be shielded by a braided sheath.

It is contemplated that the thickness of the molded silicon rubber may vary along the length of the intrauterine ribbon sensor to provide a desired balance in the flexibility along the length thereof to facilitate insertion through the vaginal channel and cervix into the uterine cavity and rec~gnizing that just prior to delivery, the head of the fetus will be generally disposed in a position partially blocking access to the uterine cavity. It is, of course, also possible to tailor the stiffness properties of the intrauterine ribbon sensor by providing plastic of differing hardness (durometer) in the segments 336 and 338 than is used in the segment 340 which lies between the proximal surface electrode $E_2$ and the male connector 302.

Rather than positioning the pressure sensor P and the surface electrodes $E_1$ and $E_2$ along with their associated conductors in a fixture and then injecting the silicon rubber so as to embed the conductors within the body of the intrauterine strip sensor, the view of FIG. 10 illustrates the possibility of fabricating the device out of a plurality of discrete segments including a distal tip electrode $E_1$, a pressure sensing module P and a connector 302 respectively coupled in end-to-end relation by means of tubing segments 342, 344 and 346. While not shown in FIG. 10, it is to be recognized that the conductors 300, 304, 316, 318, 328 and 330 are routed through the lumen of the tubular segments 342, 344 and 346 to the proximal connector 302. The tubing segments 342 and 344 will preferably be in the form of a flattened oval similar in cross-section to the device depicted in FIGS. 8 and 9 and, moreover, the segments 342, 344 and 346 may then be filled with a suitable plastic such as silicon rubber, with due consideration being paid to the durometer of the material filling the respective tubular segments to provide desired stiffness properties along the length thereof.

In the cross-sectional view of FIG. 10, the distal tip electrode $E_1$ may be formed from stainless steel or other suitable metal and includes an integrally formed stub 348 of oval cross-section dimensioned to fit within the lumen of the tube segment 342 and it would be bonded in place by an appropriate adhesive so that the exterior dimension of the electrode surface is continuous with the exterior dimensions of the tubular plastic segment 342. Similarly, the electrode $E_2$ is tubular in form and includes integrally formed stub segments 350 and 352 allowing it to be inserted between the plastic tubular segments 344 and 346 without creating a size discontinuity along the length of the ribbon sensor.

Referring next to FIGS. 11 and 12, an explanation will be given as to a preferred way of fabricating the pressure sensor segment P of the intrauterine ribbon sensor. It is seen to include a carrier member 354 also in the form of a flattened oval and having an ovalular stub 356 and 358 extending longitudinally from opposite ends thereof for mating with the tubular segments 342 and 344, respectively (FIG. 10). The carrier 354 may also be fabricated from stainless steel. However, because the operation of the sensor does not depend on the fact that the carrier 354 is conductive, it may just as well be fabricated in a molding operation from a suitable relatively non-deformable plastic, such as polysulfone resin. Supported within the carrier 354 is a sensor substrate 360 comprising a phenolic printed circuit board having a conductive pattern formed on the top surface thereof as indicated by the cross-hatching in FIG. 12. The etched paths, which are free of cross-hatching, effectively divide the conductive area into four segments. It is the internal resistance of these segments that create the compensating resistors shown o the compensation board 332 in FIG. 7.

As shown in FIG. 11, a hole 362 is formed through the thickness dimension of the printed circuit substrate board 360 and on the upper surface of the board 360 is disposed a chip 364 on the surface of which is located the piezo-resistive elements 310-313. A wire bonding technique well known in the art may be used to establish an electrical connection between the conductive pattern on the substrate 360 and the piezo-resistive elements on the chip 364. These wire bonds can be seen in FIG. 12 and are identified by numerals 365-370.

The cavity 372 surrounding the chip 364 and lying above the substrate 360 in FIG. 11 is filled with a silastic adhesive while the space 374 located beneath the substrate 360 remains empty. A vent tube 376 extends the length of the ribbon sensor and is opened to the atmosphere such that the pressure within the cavity 374 remains at atmospheric pressure. In that the port 362 passes through the substrate 360, the chip array 364 is also subjected to atmospheric pressure on the underside thereof. As such, deflection of the chip 364, as by fluid pressures applied to it via the silastic filled window 372, unbalances the bridge 314 to produce an output signal proportional to such fluid pressure.

FIG. 13 is intended to illustrate the manner in which the pressure transducer card of FIG. 12 can be disposed in the distal tip electrode $E_1$ rather than in a separate carrier such as is shown by numeral 354 in FIG. 11. In FIG. 13, electrode $E_1$ comprises a hollow conductive body 380 having a stub 382 for receiving a silastic or urethane tube segment 342 thereon. Milled through the side wall of the body 380 is a rectangular opening 384 leading to flange surfaces 386 and 388. The opening 384 is dimensioned to receive the printed circuit card 360 of FIG. 12 on which the piezoresistive chip 364 is mounted. The card 360 rests upon the flanges 386 and 388 and the portion of the cavity above it is filled with a highly compliant medium which acts as a deformable membrane. In that the body 380 is conductive, it can serve as an ECG electrode. The card 360 being an insulating substrate, the circuit pattern thereon remains isolated from the conductive body. This alternative construction obviates the need for a separate pressure transducing carrier and reduces the overall cost of the intrauterine ribbon sensor.

With no limitation intended, the overall length of the intrauterine ribbon sensor from its distal tip to its proximal connector 302 may typically be 160 mm while the distance from the tip electrode $E_1$ to the proximal electrode $E_2$ may be 60 mm with the pressure sensor P disposed midway therebetween. The overall width dimension of the intrauterine ribbon sensor at its distal end may be typically 8 mm and have a thickness of 3 mm.

The pressure transducer utilized in the present invention is extremely sensitive and has been found to produce a high frequency component due to the sound waves produced by the heart beat of the fetus and mother. It is, therefore, contemplated that by providing suitable signal processing circuitry in the monitor for discriminating between the two, it is possible to derive not only intrauterine pressure readings but heart rate information as well from the pressure transducer, thus potentially obviating the need for separate ECG surface electrodes on the ribbon sensor.

While a preferred embodiment of the invention has been shown and described herein, it can be appreciated by those skilled in the art that other embodiments of the invention not specifically described herein may be employed without departing from the spirit and scope of the invention.

What is claimed is:

1. An apparatus for monitoring intrauterine pressure pulses and fetal heart rate, comprising:

a pressure transducer diaphragm with first and second sides, said first side being in communication with said intrauterine pressure pulses;

cable means for providing a plurality of electrical conductors, at least two of said plurality of conductors being connected to said pressure transducer;

vent means for introducing atmospheric pressure to said second side of said diaphragm;

means for connecting the plurality of electrical conductors to a monitoring device; and a pair of electrode means for independently receiving electrical signals through amniotic fluid generated by the heart of a fetus, each said electrode means being located on outside surface of said cable means so as to be in electrical contact with said amniotic fluid and being positioned at a leading end of said cable means adjacent said transducer such that when said leading end is inserted into the uterus of a patient, each said electrode means senses fetal heart rate through amniotic fluid within the uterus, each said electrode means being connected to at least one of the plurality of electrical conductors such that the fetal heart rate and the intrauterine pressure may be displayed by said monitoring device.

2. An apparatus for monitoring intrauterine pressure pulses and fetal heart rate as defined by claim 1 wherein each of said electrode means comprises an electrode disposed on said cable means.

3. An apparatus for monitoring intrauterine pressure pulses and fetal heart rate as defined in claim 2 wherein said electrodes comprise metallic bands disposed about the circumference of said cable means.

4. An apparatus for monitoring intrauterine pressure pulses and fetal heart rate as defined in claim 2 wherein said electrodes are spaced a distance apart on said cable means.

5. An apparatus for monitoring intrauterine pressure pulses and fetal heart rate as defined in claim 1 wherein said pressure transducer is positioned near the leading end of the cable means and said pressure transducer fits within the diameter of said cable means.

6. An apparatus for monitoring intrauterine pressure pulses and fetal heart rate as defined in claim 1 wherein the leading end of said cable means is rounded so as to avoid tissue damage and is sufficiently small so as to be easily inserted past a fetus in the cervical region.

7. An apparatus for monitoring uterine pressure pulses and fetal heart rate as defined in claim 1 wherein means for connecting the plurality of electrical conductors comprises a plug connected to the cable means, the plug having a channel formed therein, said channel being in communication with said vent means.

8. An apparatus for monitoring intrauterine pressure pulses and fetal heart rate as defined in claim 1 further comprising a stiffener means associated with said cable means for stiffening said cable means to accommodate insertion within a body compartment of a patient.

9. An apparatus for monitoring intrauterine pressure pulses said fetal heart rate as defined in claim 1 wherein the vent means comprises a vent tube leading from said second side of said diaphragm to said means for connecting the plurality of electrical connectors, said vent tube opening to the atmosphere.

10. An apparatus for monitoring intrauterine pulses and fetal heart rate as defined in claim 1 further comprising the dielectric gel material disposed over said first side of said diaphragm, said dielectric gel material being adapted for communicating the intrauterine pressure pulses to said diaphragm.

11. An apparatus for monitoring intrauterine pressure pulses and fetal heart rate, comprising:

a pressure transducer having a diaphragm with first and second sides;

means for communicating said intrauterine pressure pulses to the first side of said diaphragm;

means for venting the second side of said diaphragm to atmospheric pressure;

cable means for providing a plurality of individual conductors at least two of the individual conductors being connected to said pressure transducer;

means for connecting the individual conductors to monitoring equipment; and a first pair of electrodes spaced one from the other and disposed on said cable means on an exterior surface at a leading end thereof, said first pair of electrodes being adapted for receiving independent of one another electrical signals through amniotic fluid generated by the heart of a fetus when inserted into the uterus of a patient, each of said electrodes being individually connected to at least one of said plurality of individual conductors such that the fetal heart rate may be displayed by said monitoring equipment simultaneously with the intrauterine pressure pulses.

12. An apparatus for monitoring intrauterine pressure pulses and fetal heart rate as defined in claim 1 wherein said electrodes comprises metallic bands disposed about the circumference of said cable means.

13. An apparatus for monitoring intrauterine pressure pulses and fetal heart rate as defined in claim 11 wherein the pressure transducer fits within the diameter of said cable means.

14. An apparatus for monitoring intrauterine pressure pulses and fetal heart rate as defined in claim 11 wherein the pressure transducer comprises substrate means onto which said diaphragm is mounted and cap means joined to said substrate means so as to form a protective cover over said diaphragm.

15. An apparatus for monitoring intrauterine pressure pulses and fetal heart rate as define din claim 11 wherein the leading end of said cable means is rounded and small so as to avoid uterine wall perforation, irritation or placental abruption.

16. An apparatus for monitoring intrauterine pressure pulses and fetal heart rate as defined in claim 11 wherein said means for connecting the plurality of electrical conductors comprises a plug connected to the cable means, the plug having a channel formed therethrough in communication with said means for venting.

17. An apparatus for monitoring intrauterine pressure pulses and fetal heart rate as defined in claim 11 further comprising a stiffener means associated with said cable means for stiffening said cable means to accommodate insertion within a body compartment to a patient.

18. An apparatus for monitoring intrauterine pressure pulses and fetal heart rate as define din claim 11 further comprising a lumen disposed in said cable means, said lumen having an opening disposed at a position along the length of said cable means.

19. An apparatus for monitoring intrauterine pressure pulses and fetal heart rate as defined in claim 11 wherein the means for ·enting comprises a vent tube leading from said second side of said diaphragm to said means for connecting the plurality of electrical connectors, said vent tube opening to the atmosphere.

20. An apparatus for monitoring intrauterine pressure pulses and fetal heart rate as defined in claim 11 wherein the means for communicating comprises a dielectric gel material disposed over said first side of said diaphragm, said dielectric gel material being adapted for communicating the intrauterine pressure pulses to said diaphragm.

21. An apparatus for sensing intrauterine pressure and fetal electrocardiogram comprising:
  (a) a housing having a distal end and a proximal end and further having a prefilled pressure cavity sealed with a highly compliant membrane;
  (b) a first electrode mounted on the housing;
  (c) a second electrode mounted on the housing suitably distanced from the first electrode such that ECG signals are sensed in cooperation with the first electrode;
  (d) means for connecting the first and second electrodes to a means for monitoring the ECG signals;
  (e) pressure tubing embedded in the housing and connected to the pressure cavity and prefilled with a bubble-free, sterile, biocompatible liquid and completely sealed and terminating at the proximal end of the housing in a Luer fitting.

22. A system for sensing and monitoring intrauterine pressure and fetal electrocardiogram comprising:
  (a) a housing having a distal end and a proximal end and further having a prefilled pressure cavity sealed with a highly compliant membrane;
  (b) a first electrode mounted on the housing;
  (c) a second electrode mounted on the housing suitably distanced from the first electrode such that ECG signals are sensed in cooperation with the first electrode;
  (d) means for connecting the first and second electrodes to a means for monitoring the ECG signals;
  (e) pressure tubing embedded in the housing and connected to the pressure cavity and prefilled with a bubble-free, sterile, biocompatible liquid and completely sealed and terminating at the proximal end of the housing in a Luer fitting;
  (f) means for monitoring fetal ECG connected to the first and second electrodes; and
  (g) means for monitoring intrauterine pressure connected to the Luer fitting.

23. A sensor for detecting electrical signals and pressure variations within a uterus for presentation to a signal monitoring means comprising:
  (a) an elongated flexible tubular housing having a flattened ovalular cross-section, a proximal end and a distal end;
  (b) at least one surface electrode mounted on said tubular housing near said distal end and a first conductor connected to said surface electrode and extending through a first lumen of said tubular housing to said proximal end;
  (c) a pressure transducer assembly including a substrate having piezoresistive elements disposed thereon and mounted in said housing so as to be exposed to fluid pressure forces when immersed in a fluid medium;
  (d) further conductors electrically coupled to said piezoresistive elements and extending through said first lumen of said tubular housing to said proximal end; and
  (e) electrical connector means affixed to said proximal end of said housing and connected to said first and further conductors for facilitating coupling of said sensor to said signal monitoring means.

24. The sensor as in claim 23 wherein said pressure transducer comprises a plurality of piezoresistive elements supported on a deformable substrate and joined together as a Wheatstone bridge, said deformable substrate being affixed to a printed circuit board, means bonding said piezoresistive elements to said printed circuit board and means connecting said further conductors to said printed circuit board.

25. The sensor as in claim 24 and further including means for venting one side of said deformable substrate to a reference pressure.

26. The sensor as in claim 25 wherein said means for venting comprises a second lumen extending from said proximal end of said tubular housing to said zone.

27. The sensor as in claim 23 wherein said elongated flexible tubular housing comprises a plurality of segments joined together in end-to-end relationship thereby providing distal segments.

28. The sensor as in claim 27 wherein one of said plurality of segments comprises said surface electrode.

29. The sensor as in claim 27 wherein one of said plurality of segments supports said printed circuit board.

30. The sensor as in claim 27 wherein alternate ones of said plurality of segments are formed from silicon rubber exhibiting predetermined degrees of hardness whereby the distal most silicon rubber segments are of lesser hardness than more proximal ones of said silicon rubber segments.

31. The sensor as in claim 27 wherein one of said segments includes said pressure transducer assembly.

32. The sensor as in claim 31 wherein said one of said segments including said pressure transducer also comprises said surface electrode.

* * * * *